US00PP24038P3

(12) United States Plant Patent
Jauchen

(10) Patent No.: US PP24,038 P3
(45) Date of Patent: Nov. 26, 2013

(54) MINIATURE ROSE PLANT 'PACNINETYSEVEN'

(50) Latin Name: *Rosa hybrida*
Varietal Denomination: PACninetyseven

(76) Inventor: Daniel Jauchen, Santa Barbara, CA (US)

( * ) Notice: Subject to any disclaimer, the term of this patent is extended or adjusted under 35 U.S.C. 154(b) by 100 days.

(21) Appl. No.: 13/317,581

(22) Filed: Oct. 24, 2011

(65) Prior Publication Data

US 2013/0104267 P1 Apr. 25, 2013

(51) Int. Cl.
*A01H 5/00* (2006.01)

(52) U.S. Cl.
USPC ..... Plt./118

(58) Field of Classification Search
USPC ..... Plt./118
See application file for complete search history.

*Primary Examiner* — June Hwu

(57) ABSTRACT

A new miniature rose plant which has abundant, yellow colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Botanical designation: *Rosa hybrida.*
Variety denomination: 'PACninetyseven'.

BACKGROUND OF THE INVENTION

The present invention constitutes a new and distinct variety of miniature rose plant, which was developed by artificially pollinating an unnamed seedling (not patented) with an unnamed seedling (not patented). The two parents were crossed in the summer of 2002 and the resulting seed was sown in December 2002, in a controlled glasshouse environment. Out of these seedlings one seedling was selected, as the new variety and named 'PACninetyseven'. The new rose may be distinguished from its seed parent, an unnamed seedling, by the following combination of characteristics:

1. 'PACninetyseven' has small, double full bloom flowers, while the unnamed seedling has small double flowers.
2. 'PACninetyseven' has yellow colored petals, while the unnamed seedling has white petals.

The new variety may distinguish from its pollen parent, an unnamed seedling, by the following combination of characteristics:

1. 'PACninetyseven' has small, double full bloom flowers, while the unnamed seedling has medium double flowers.
2. 'PACninetyseven' has yellow colored petals, while the unnamed seedling has yellow-peach petals.

BRIEF SUMMARY OF THE INVENTION

Initial asexual reproduction of 'PACninetyseven' by cuttings was first done in Santa Barbara, Calif., USA. This initial and other subsequent propagation conducted in controlled environments have demonstrated that the characteristics of 'PACninetyseven' are true to type and are transmitted one generation to the next. 'PACninetyseven' is a low and compact miniature rose with good vigor. The objective of the hybridization of this rose variety for commercial greenhouse culture was to create a new and distinct variety with:

1. Uniform and abundant flowers with good keeping ability;
2. Attractive long lasting foliage and compact growth;
3. Year round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type, known to the inventor, and distinguish 'PACninetyseven' from all other varieties of which I am aware.

The seeds from hybridization were planted in a controlled environment and evaluations were conducted on the resulting plants. 'PACninetyseven' was selected by, Daniel Jauchen, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'PACninetyseven'. Specifically illustrated in the drawings:

1: Young shoot.
2: Bud before opening the sepals.
3: Bud at the stage of opening the sepals.
4: Bud at the stage of opening the petals.
5: Flower during course of opening.
6: Open flower—plan view—obverse.
7: Open flower—plan view—reverse.
8: Fully open flower-plan view-obverse.
9: Fully open flower-plan view-reverse.
10: Receptacle showing stamens and pistils.
11: Receptacle showing pistils (stamens and sepals removed).
12: Flower petals, detached—inner surface.
13: Flower petals, detached—outer surface.
14: Bare stem exhibiting thorns and flower attachment.
15: Three leaflets upper side.
16: Three leaflets reverse side.

17: Five leaflets upper side.
18: Five leaflets reverse side.

DETAILED BOTANICAL DESCRIPTION OF THE VARIETY

The following is a detailed description of the Miniature Rose: *Rosa hybrida* 'PACninetyseven'.

The following observations, measurements, values and comparisons describe plants grown in glass houses in Santa Barbara, Calif., USA.

The age of the observed plants were 3 months after propagation by cuttings, and produced as flowering pot plants in container of 10 centimeter in diameter. Environmental conditions in the cultivation area for the observed plants, has been temperatures from 64 to 78 degree Fahrenheit, and 10 to 20 hours day length with assimilation light. Light levels from 600 foot candle to 6000 foot candle. The relative humidity has been ranging from 50 to 85%.

Color references are made using The Royal Horticultural Society (London, England) Colour Chart, 1995, except where common terms of color are used. For a comparison, the nearest existing rose variety is 'POULsun', a rose variety described and illustrated in U.S. Plant Pat. No. 9,716.

Chart 1 details several physical characteristics of 'PACninetyseven' and 'POULsun'.

CHART 1

| | 'PACninetyseven' | 'POULsun' |
|---|---|---|
| Petal color, Upper surface | Yellow Group 10B | Yellow Group 13A |
| Petal color, Reverse surface | Yellow Group 11A-B | Yellow Group 13B |
| Petal count | 65 to 70 | 30 to 35 |

Parents: Unnamed seedling times unnamed seedling.

Classification:

*Botanical.*—Rosa hybrida.

*Commercial.*—Miniature.

Plant:

*Plant growth.*—Moderately vigorous. Grows compact upright to bushy. When grown as 10 cm pot plant, the average height of the plant itself is 18 cm to 20 cm, and average width is 20 cm. When grown as a 15 cm pot plant, the average height of the plant itself is 22 cm to 27 cm, and average width is 30 cm.

Stem:

*Color.*—Young wood: Green Group 137C, with intonations of Red-Purple group 61A. Older wood: Green Group 137C.

*Thorns.*—Incidence: 7 to 8 per stem. Size: 5 to 6 mm. Form: Deep concave. Color: Red-Purple group 61A.

*Surface.*—Young wood: Smooth. Older wood: Smooth.

*Stem diameter.*—Length: 165 mm. Width: 2 mm to 3 mm.

*Internode length.*—25 mm to 45 mm.

*Numbers of internodes.*—4 to 6.

Plant foliage: Leaves arranged alternately, compound with 3 to 5 leaflets per leaf, generally symmetrical, abundant, and flat in aspect. Stipules at petiole. base.

*Quantity of leaves.*—5 to 6 per lateral branch.

*Leaf size.*—Length 35 mm to 55 mm, Width 30 mm to 45 mm.

*Petioles.*—Color: Yellow-Green Group 152A, with intonations of Red-Purple Group 60A. Margins: Entire. Length: about 10 mm. Diameter: about 1 mm.

*Stipules.*—Size: Length 4 mm to 5 mm, Width 1 mm to 1.5 mm. Upper and lower surface: Smooth. Color for upper surface: Green Group 139B. Color for lower surface: Green Group 138A. Margins: Entire. Apex shape: Spinose.

*Rachis.*—Color: Yellow-Green Group 152A, with intonations of Red-Purple Group 60A. Margins: Entire. Length: 10 mm to 15 mm. Diameter: 0.5 mm to 1 mm.

*Pedicel.*—Color: Yellow-Green 146B. Texture: Glabrous all around. Size: Length: 15 mm to 20 mm. Width: 3 mm to 3.5 mm.

*Leaflets.*—Edge: Serrated. Serration: Single. Shape: Ovate with acute apex and obtuse base. Leaf upper and lower texture: Smooth. Appearance: Dull. Size: length: 20 mm to 40 mm, width: 10 mm to 20 mm. Color: Young foliage: Upper surface: Green Group 135A. Lower surface: Green Group 138B. Color: Mature foliage: Upper surface: Green Group 137A. Lower surface: Green Group 138B. Leaf vein color: Upper surface: Green Group 135C. Reverse surface: Green Group 134A.

Inflorescence:

*Blooming habit.*—Recurrent.

*Number of flowers.*—Generally one to three buds per flowering stem.

*Average size.*—Length: 17 mm. Width: 12 mm.

*Peduncle.*—Color: Green Group 141C. Texture: Smooth. Length: 20 mm to 35 mm Diameter: 3 mm to 4 mm. Strength: Upright.

*Receptacle.*—Surface: Smooth, glabrous. Shape: Funnel-shaped. Size: height 5 mm to 7 mm, width 8 mm to 10 mm. Color: Green Group 143C.

*Sepals.*—Quantity: Five. Shape: Narrowly ovate with acute tip. Upper and lower texture: Leathery. Margin: Foliaceous appendages on three of the five sepals. Appearance: Dull. Color: Upper surface: Green Group 141B. Reverse surface: Green Group 141B. Size: Length 20 mm to 25 mm, width 7 mm to 8 mm.

*Buds.*—Size: Height 10 mm to 15 mm, diameter 13 mm to 15 mm, Upon opening. Shape: Ovoid. Color: at ¼ opening, Yellow Group 5A.

*Flower.*—Duration: As a pot plant, flowers last from 10 to 15 days. Fragrance: Slightly spicy. Size: 35 mm to 45 mm in diameter. Depth: 15 mm to 20 mm. Form: Shape of flower when viewed from the side: Upon opening: Cupped to ovoid. Open flower: Flat rosette. Color: Petals, upon opening: Upper surface: Yellow-Group 10B. Reverse surface: Yellow-Group 11A-B. Petals after opening: Upper surface: Yellow-Group 10B. Reverse surface: Yellow-Group 11A-B. General tonality: On open flower: Third day: Yellow-Group 11A-B. Afterwards: Yellow-Group 11A-B.

*Petals.*—Petal reflex: Outermost petals reflex backwards at opening. Fully open all petals reflex backwards. Texture: Smooth. Petal edge: Entire. Petal count: 65 to 70 on the average per flower. Petal size: Length 20 mm to 22 mm. Width 25 mm to 30 mm. Shape: Outer petals: Round — ovate. Inner petals: Ovate. Apex: Rotundate. Base: Obtuse to rotundate.

*Petaloids.*—None.

*Reproductive organs.*—Stamen number: Approximately 4 to 8 on average per flower (Stamen converted into petals, mostly pistils remain.). Stamens length: 4 mm to 5 mm. Pollen: Color: Yellow-Orange Group 18C. Abundance: Heavy. Anthers: Size: 1 mm to 1.5 mm Color: Yellow-Orange Group 18C. Shape: Oblong. Filaments: Size: 3 mm to 4 mm. Color: Yellow Group 12D. Pistils number: Approximately 25 to 30 on average per flower. Stigmas: Location: Protrude more than the anthers. Color: white group 155C. Styles: Color: White Group 155C. Length: 6 mm to 7 mm.

Development:

*Vegetation.*—Dense.

*Blooming.*—Abundant.

*Aptitude to bear fruit.*—Poor.

*Resistance to diseases.*—Above average resistance to powdery mildew and *Botrytis* under normal growing conditions in Santa Barbara, Calif., USA. Hips/seeds has not been observed due to that the plant has never been grown to the stage of seed development, due to the fact, that the variety is developed for use as a flowering pot plant only.

*Winter hardiness & drought/heat tolerance.*—Due to the fact, that this variety is a potted flowering plant, developed indoor use only, the plant is not tested for winter hardiness or drought/heat tolerance.

The invention claimed is:

1. A new and distinct variety of Rose plant of the miniature class, substantially as herein illustrated and described as a distinct and novel rose variety due to its abundant yellow flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

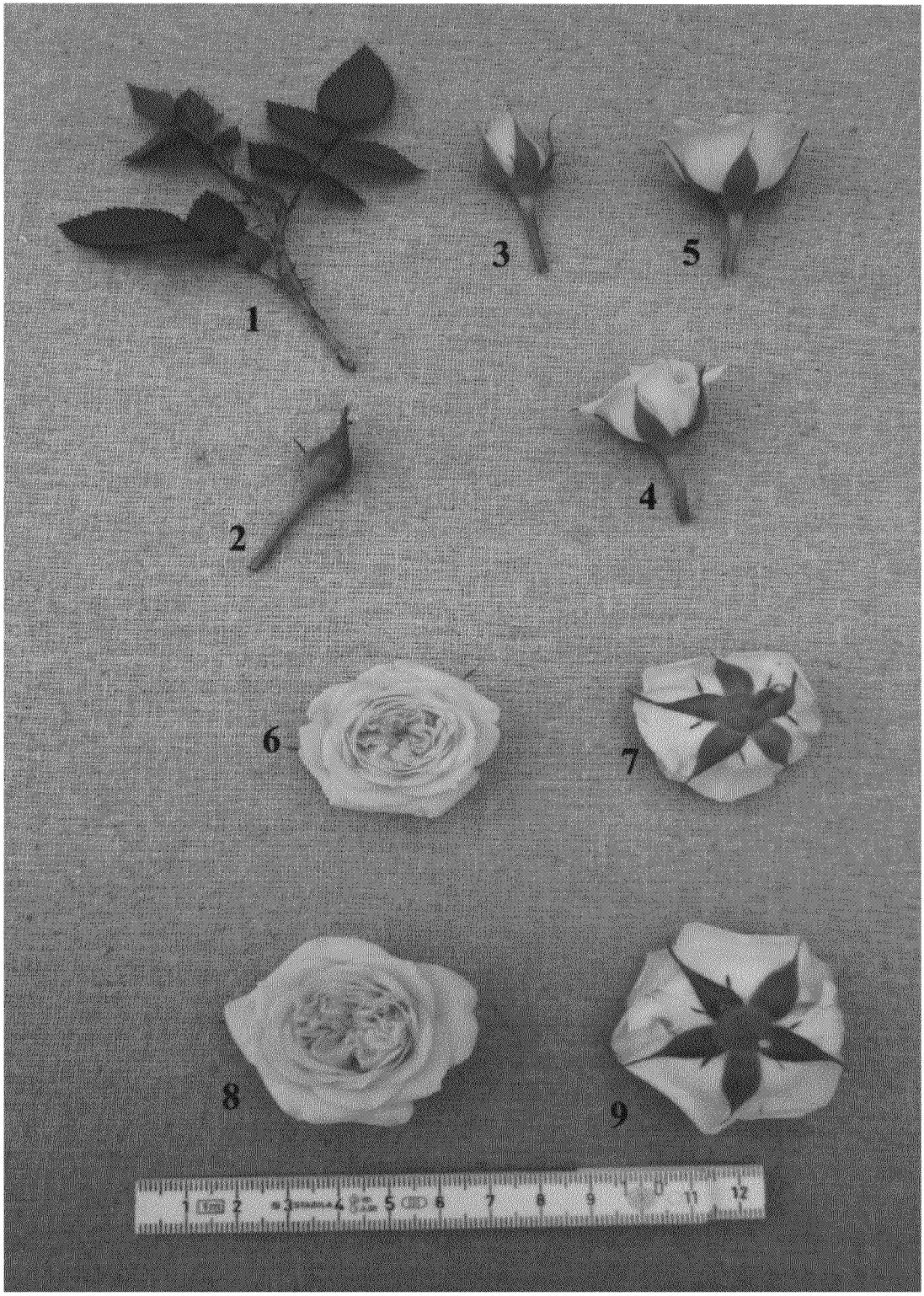
1
2
3
4
5
6
7
8
9

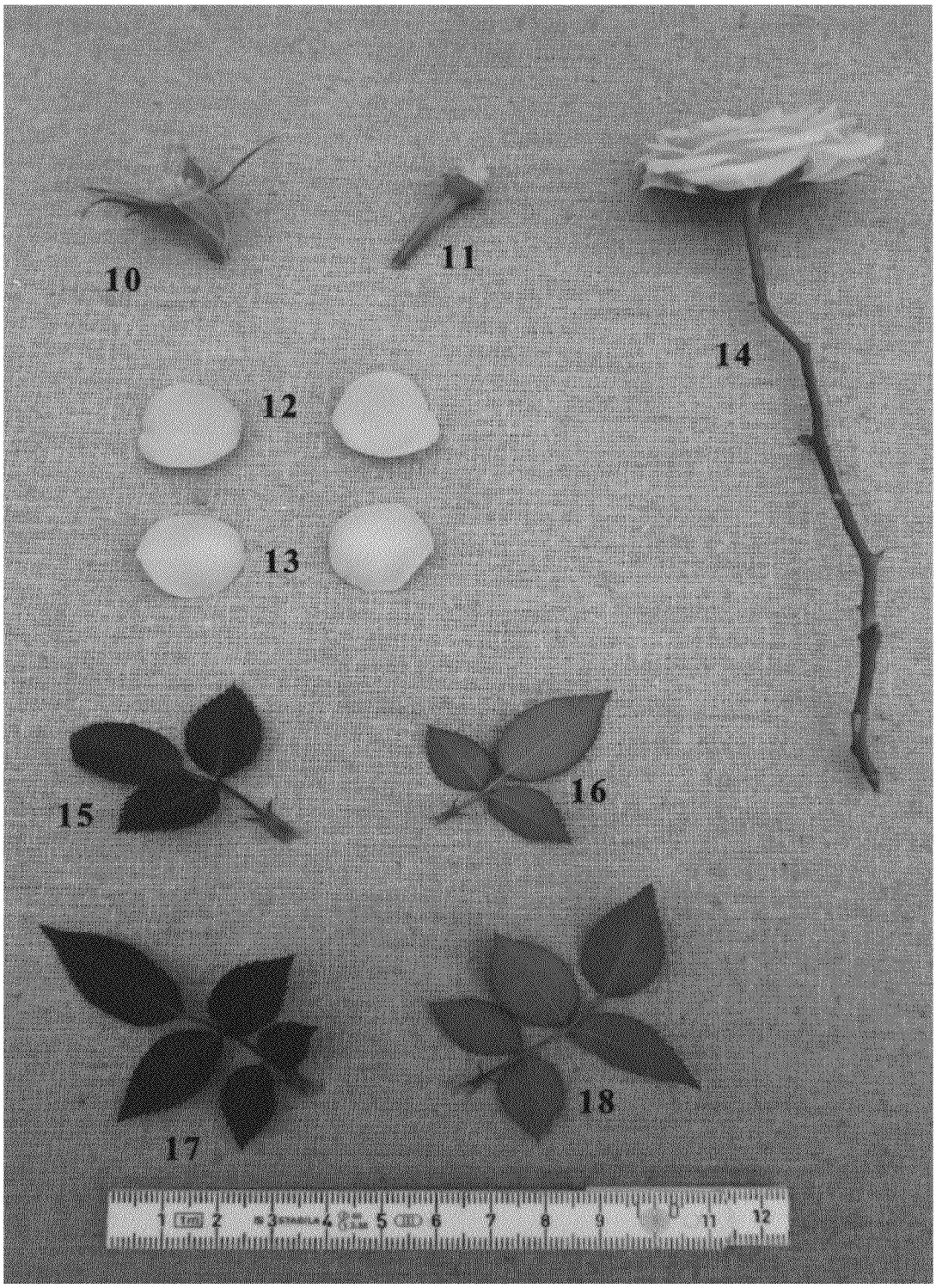
10
11
12
13
14
15
16
17
18